United States Patent [19]

Möhring et al.

[11] 4,258,222
[45] Mar. 24, 1981

[54] PROCESS FOR THE PRODUCTION OF LOW MOLECULAR WEIGHT POLYHYDROXYL COMPOUNDS

[75] Inventors: Edgar Möhring, Bergisch-Gladbach; Hanns P. Müller; Kuno Wagner, both of Leverkusen, all of Fed. Rep. of Germany

[73] Assignee: Bayer Aktiengesellschaft, Leverkusen, Fed. Rep. of Germany

[21] Appl. No.: 55,656

[22] Filed: Jul. 6, 1979

[30] Foreign Application Priority Data

Jul. 19, 1978 [DE] Fed. Rep. of Germany ....... 2831719

[51] Int. Cl.$^3$ .............................................. C07C 31/18
[52] U.S. Cl. .................................. 568/863; 521/155; 528/300; 528/405
[58] Field of Search ......................................... 568/863

[56] References Cited

U.S. PATENT DOCUMENTS

| | | | |
|---|---|---|---|
| 2,224,910 | 12/1940 | Hanford et al. | 568/862 |
| 2,269,935 | 1/1942 | Hanford et al. | 568/391 |
| 2,271,083 | 1/1942 | Lorand | 568/863 |
| 2,276,192 | 3/1942 | Hanford et al. | 568/862 |
| 2,775,621 | 12/1956 | Maclean et al. | 568/863 |

FOREIGN PATENT DOCUMENTS

| | | | |
|---|---|---|---|
| 725842 | 10/1942 | Fed. Rep. of Germany. | |
| 514342 | 11/1939 | United Kingdom | 568/863 |
| 514693 | 11/1939 | United Kingdom | 568/863 |
| 1542980 | 3/1979 | United Kingdom. | |

OTHER PUBLICATIONS

Orthner et al, "Biochem. Zeitung" 259, 30 (1933), translation.

*Primary Examiner*—Joseph E. Evans
*Attorney, Agent, or Firm*—Gene Harsh; Joseph C. Gil

[57] ABSTRACT

The instant invention is directed to a process for the production of low molecular weight polyhydric alcohols by hydrogenating formose solutions in the presence of metal catalysts comprising (a) introducing an at least 20% solution of formose, of which the pH-value was adjusted before hydrogenation to a value of from 7.5 to 12.5, in batches into a first reactor in a manner such that the content of reducible groups, determined as carbonyl groups, in the reactor does not exceed a level of 2% by weight;

(b) hydrogenating the solution in batches in the presence of a total quantity of a first catalyst of from $10^{-4}$ to $5.10^{-2}$% by weight, based on the total quantity of starting product to be reduced, the amount of said first catalyst remaining constant in the reactor, said first catalyst being selected from the group consisting of metals having atomic numbers of from 23 to 29 and mixtures thereof, said metals, being in elemental and/or oxidic form;

(c) withdrawing the reaction product in batches from the first reactor after the content of reducible groups, determined as carbonyl groups, has fallen to below 1.5% by weight;

(d) adjusting the pH-value of the reaction product to between 3 and 7;

(e) introducing said reaction product in batches into a second reactor;

(f) hydrogenating said reaction product in batches in the presence of a total quantity of a second catalyst of from $10^{-5}$ to $10^{-1}$% by weight of active metal, based on the total quantity of starting product to be reduced, the amount of said second catalyst remaining constant in the second reactor, said second catalyst being selected from the group consisting of metals having atomic numbers of 44, 45, 75 and 77, compounds thereof, and mixtures thereof; and (g) after a residence time of from 5 minutes to 4 hours withdrawing the reaction product of the second hydrogenation stage in batches from the second reactor.

12 Claims, No Drawings

PROCESS FOR THE PRODUCTION OF LOW MOLECULAR WEIGHT POLYHYDROXYL COMPOUNDS

BACKGROUND OF THE INVENTION

This invention relates to an improved process for the production of low molecular weight polyalcohols by the catalytic hydrogenation, in two stages of a mixture of different low molecular weight hydroxy aldehydes, hydroxy ketones and polyhydric alcohols of the type formed in the autocondensation of formaldehyde. (This type of mixture will be referred to hereinafter as "formose"). The invention also relates to the use of these polyalcohols for the production of polyurethane plastics.

Since the work of Butlerow and Loew [Ann. 120, 295 (1861) and J. prakt. Chem. 33, 321 (1886)] in the previous century, it has been known that hydroxy aldehydes, hydroxy ketones and polyhydric alcohols are formed in the autocondensation of formaldehyde hydrate (formose synthesis) under the influence of basic compounds such as, for example, calcium or lead hydroxide. Formose has been repeatedly synthesized ever since.

In this connection, reference is made for example of Pfeil, Chem. Berichte 84, 229 (1951), Pfeil and Schroth, Chemische Berichte 85, 303 (1952), R. D. Partridge and A. H. Weiss, Carbohydrate Research 24, 29–44 (1972), Emil Fischer, Formoses of Glycerol Aldehyde and Dioxy Acetone, German Pat. Nos. 822,385; 830,951 and 884,791; U.S. Pat. Nos. 2,121,981; 2,224,910; 2,269,935 and 2,272,378 and British Pat. No. 513,708. These known processes are attended by certain disadvantages (poor volume/time yields, colored secondary products). In recent years, however, new processes have been developed by which it is possible, using conventional catalysts, to obtain high yields of substantially colorless formoses free from troublesome secondary products.

In one of these new processes, the condensation of formaldehyde hydrate is carried out in the presence of soluble or insoluble lead(II)salts or lead(II)ions fixed to high molecular weight substrates, as catalysts and a mixture of hydroxy aldehydes, hydroxy ketones, and polyhydric alcohols of the type formed in the condensation of formaldehyde hydrate, as co-catalyst. In this process, the reaction temperature is generally in the range from 70° to 110° C. and preferably in the range from 80° to 100° C. The pH-value of the reaction solution is adjusted to between pH 6.0 and 8.0 and preferably to between pH 6.5 and 7.0 up to a conversion of from 10 to 60%, preferably from 30 to 50%. Thereafter, the pH is adjusted to between pH 4.0 and 6.0 and preferably to between pH 5.0 and 6.0 by the controlled addition of an inorganic or organic base. By this special control of pH and by subsequent cooling, it was surprisingly possible, despite different residual formaldehyde contents (from 0 to 10% by weight and preferably from 0.5 to 6.0% by weight), to vary reproducibly the product distribution of the corresponding polyol, hydroxy aldehyde and hydroxy ketone mixtures.

After the autocondensation of the formaldehyde hydrate has been interrupted by cooling and/or by deactivation of the lead-containing catalyst with acids, the catalyst and any water present in the products, are removed. For fuller particulars, reference is made to German Offenlegungsschriften Nos. 2,639,084 and 2,732,077.

According to German Offenlegungsschrift No. 2,714,084, another possibility of producing highly concentrated colorless formoses in high volume-time yields is to condense aqueous formalin solutions and/or paraformaldehyde dispersions in the presence of a soluble or insoluble metal catalyst and a co-catalyst produced by the partial oxidation of a dihydric or polyhydric alcohol containing at least two adjacent hydroxyl groups and having a molecular weight of from 62 to 242 or of a mixture of alcohols of this type. The pH-value of the reaction solution is kept between 6.0 and 9.0 up to a conversion of from 5 to 40% by the controlled addition of a base. The pH is subsequently adjusted to between 4.5 and 8.0 until the condensation reaction is terminated, so that it is then lower by 1.0 to 2.0 units than in the first phase of the reaction. The reaction is subsequently terminated by deactivating the catalyst at a residual formaldehyde content of from 0 to 10% by weight and the catalyst is removed.

Formoses of high quality can also be obtained by condensing formaldehyde in the presence of a metal catalyst and more than 10% by weight, based on formaldehyde, of one or more dihydric or polyhydric low molecular weight alcohols and/or relatively high molecular weight polyhydroxyl compounds (cf. German Offenlegungsschrift No. 2,714,104).

According to German Offenlegungsschrift No. 2,721,186, it is particularly economical to use synthesis gases containing formaldehyde directly, i.e. without the necessity of first forming aqueous formalin solutions or paraformaldehyde. In this regard, the synthesis gases, such as are formed in the production of formaldehyde on an industrial scale, are introduced continuously or in batches at temperatures of from 10° to 150° C. into an absorption liquid which consists of water, monohydric or polyhydric low molecular weight alcohols and/or relatively high molecular weight polyhydroxyl compounds and/or compounds capable of enediol formation as co-catalysts and/or soluble or insoluble metal compounds which may be fixed to high molecular weight substrates as catalysts and which have a pH-value of from 3 to 10. The formaldehyde is directly condensed in situ in the absorption liquid (or even in a following reaction tube or a following cascade of stirrer-equipped vessels). The autocondensation of the formaldehyde is terminated at a residual formaldehyde content in the reaction mixture of from 0 to 10% by weight by cooling and/or by deactivating the catayst with acids. Finally, the catalyst is removed.

For numerous applications, mixtures of hydroxy aldehydes, hydroxy ketones and polyalcohols of the type obtained by the processes described above or by conventional processes, have to be converted into mixtures of polyalcohols by reduction of the carbonyl groups (polyol mixtures such as these obtained by the reduction of formose are referred to hereinafter as "formitols"). For example, formose can be directly reduced from aqueous solution with sodium borohydride at temperatures as low as room temperature (cf. R. D. Partridge, A. H. Weis and D. Todd, Carbohydrate Research 24 (1972), 42). Reduction may also be carried out electrochemically.

Processes for the catalytic hydrogenation of sugars and of formose are widely known. The quantities and types of catalysts used differ widely according to the procedure adopted. Thus, L. Orthner and E. Gerisch (Biochem. Zeitung 259, 30 (1933)) described a process for the catalytic hydrogenation of formose, in which a 4% aqueous formose solution is hydrogenated with 170% by weight, based on formose, of Raney nickel in a reaction carried out over a period of 7 to 8 hours at 130° C. under a hydrogen pressure of 120 bars. A process such as this is of course economically unsatisfactory.

U.S. Pat. No. 2,269,935 describes a process in which a solution containing approximately 40% by weight of formose is hydrogenated with 20% by weight of nickel catalyst in a reaction carried out at 120° C. in the acid pH-range under a hydrogen pressure of from 600 to 620 bars. The disadvantage of this procedure lies not only in the high working pressure, but also in the low pH-value which has to be maintained and which leads to products which are colored green by nickel ions.

U.S. Pat. No. 2,224,910 describes a process for the hydrogenation of formose in which a 40% formose solution is hydrogenated with 30% by weight of Raney nickel, based on formose, in a reaction carried out over a period of 4 hours at a pH-value of 7 under a hydrogen pressure of from 140 to 210 bars. This process is also unsatisfactory due to heavy catalyst usage and the long reaction time involved.

Further hydrogenation processes are described in German Pat. Nos. 705,274; 725,842; 830,951; and 1,004,157 and in U.S. Pat. Nos. 2,271,083; 2,272,378; 2,276,192; 2,760,983 and 2,775,621. However, all of these processes are attended by one or more of the following disadvantages: heavy outlay on apparatus and difficult handling due to high hydrogen pressures; heavy outlay on catalyst, based on the hydrogenated product (10 to 200% by weight); and, colored products because of long hydrogenation times (1 to 10 hours).

One feature common to all hitherto known processes is the use of metal or, in some cases, noble metal catalysts. Raney nickel in particular is used, although it only develops its full activity in the alkaline range. However, since formose shows a tendency towards caramellization in alkaline medium and highly discolored products are formed, conventional processes are generally carried out in the weakly acid or neutral pH-range rather than in the alkaline pH-range.

According to the process described in U.S. application Ser. No. 965,645, filed on Dec. 1, 1978, it is possible to hydrogenate formose solutions (optionally in admixture with other natural and/or synthetic sugars) in a strongly alkaline medium in a fast reaction, with minimal outlay on catalyst, under hydrogen pressures of from 100 to 200 bars and at temperatures of from 50° to 250° C. to form colorless solutions of polyol mixtures. In the polyol mixtures thus obtained, the proportion of low molecular weight $C_2$-, $C_3$-, and $C_4$-alcohols is considerably greater than in the formitols obtained by conventional processes. This new process is characterized in that a more than 20% formose solution is pumped in batches into a reactor, which has a temperature of from 100° to 200° C., at such a rate that the concentration of the groups to be reduced does not exceed 2% by weight. Hydrogenation is carried out at a pH of 7.5–12.5 with from $10^{-4}$ to $5.10^{-2}\%$ by weight of catalyst (based on the entire formose) and under a hydrogen pressure of from 50 to 300 bars. The catalysts used are in particular metals having atomic numbers of from 23 to 29 (and particularly Raney nickel). However, when the colorless formitol solutions thus produced are concentrated, for example by thin layer distillation in vacuo, they frequently turn yellow in color for reasons as yet unexplained. In this respect, it does not matter how the formose solution was produced and under what conditions it was hydrogenated.

DESCRIPTION OF THE INVENTION

It has now surprisingly been found that discoloration can be completely avoided in the concentration of formitol solutions by adopting a special procedure for hydrogenation. In a first stage, hydrogenation is carried out in an alkaline medium and, in a second stage, is completed in a neutral to acid medium, preferably using ruthenium, rhodium and/or iridium catalysts.

Accordingly, the present invention relates to a process for the production of low molecular weight polyhydric alcohols by hydrogenating formose solutions in the presence of metal catalysts comprising (a) introducing an at least 20% by weight, preferably more than 35% and, with particular preference, more than 45% solution of formose, of which the pH-value was adjusted immediately before the hydrogenation reaction to a value in the range from 7.5 to 12.5 and preferably in the range from 8.5 to 11.5, in batches into a first reactor, preferably maintained at a temperature of from 100° to 200° C. and, most preferably, from 140° to 190° C., in such a manner that the content of reducible groups (determined as carbonyl groups) in the product mixture inside the reactor does not exceed a level of 2% by weight;

(b) hydrogenating the solution in batches in the presence of a total quantity of a first catalyst of from $10^{-4}$ to $5.10^{-2}\%$ by weight, based on the total quantity of starting product to be reduced, the amount of said first catalyst remaining constant in the reactor; said first catalyst being selected from the group consisting of metals having atomic numbers of from 23 to 29 and mixtures thereof, said metals being in elemental and/or oxidic form;

(c) withdrawing the reaction product in batches from the reactor after the content of reducible groups (determined as carbonyl groups) has fallen to below 1.5% by weight and preferably to 0.5% by weight;

(d) adjusting the pH-value of the reaction product to between 3 and 7 and preferably to between 4 and 6.5;

(e) introducing said reaction product in batches into a second reactor, preferably maintained at a temperature of from 50° to 250° C. and, most preferably, at from 100° to 200° C.;

(f) hydrogenating said reaction product in batches in the presence of a total quantity of a second catalyst of from $10^{-5}$ to $10^{-1}\%$ by weight of active metal, based on the total quantity of starting product to be reduced, the amount of said second catalyst remaining constant in the reactor, said second catalyst being selected from the group consisting of metals having atomic numbers of 44, 45, 75 and 77, compounds thereof, and mixtures thereof; and (g) after a residence time of from 5 minutes to 4 hours, (preferably from 10 minutes to 90 minutes), the product is withdrawn in batches from the second reactor.

The process according to the invention is carried out with particular advantage as follows:

The quantity of the first catalyst, preferably Raney nickel, which is to be used for hydrogenating the entire batch is introduced into water in a pressure reactor. The reactor is then filled with hydrogen gas up to a working pressure of from 50 to 300 bars and subsequently heated to the hydrogenation temperature of from 80° to 220° C.

3 to 30 times by weight and preferably 5 to 20 times the quantity of formose solution, based on catalyst, is then slowly pumped in (i.e. at a rate such that approximately one sixth of the reactor volume is filled in 3 minutes to 2 hours and preferably in 5 to 30 minutes). The mixture is then left to hydrogenate for half to 4 times the time required for pumping in the material. A quantity of reaction mixture corresponding to the quantity of formose solution pumped in is then removed under pressure through a steel jacket frit, the catalyst remaining in the reactor. A new batch is then pumped into the reactor and treated in the same way as the first batch. All further batches are also treated in the same way. Following acidification, each batch which was passed through this first reactor is preferably immediately introduced into the second reactor.

In the second reactor, the total quantity of the second catalyst (which consists of 1 to 10% by weight, preferably 3 to 8% by weight, based on the total catalyst weight, or ruthenium on a support, such as carbon or silicate) which is required for hydrogenating the total quantity of prehydrogenated formose solution is also introduced into water. The reactor is filled with hydrogen gas up to a working pressure of from 50 to 300 bars and is subsequently heated to the hydrogenation temperature of from 50° to 250° C. The formose solution prehydrogenated in the first reactor is preferably introduced by slowly pumping in from 50 to 5000 times, preferably from 100 to 2000 times, the quantity of hydrogenated formose solution, based on active catalyst metal (i.e. at a rate such that approximately one sixth of the reactor volume is filled in 3 minutes to 2 hours and preferably in 5 to 30 minutes). The mixture is then left to hydrogenate for half to 20 times the time required for pumping in the material. The same quantity of reaction product is then removed under pressure through a steel jacket frit, the catalyst remaining in the reactor. The next batch coming from the first reactor is then pumped into the second reactor and is treated in exactly the same way as the first batch. All further batches are also treated in the same way.

This two-stage batch-type pumping hydrogenation according to the invention provides extremely long catalyst service lives both in the first stage, preferably carried out with Raney metal catalysts, in alkali medium and also in the second stage, carried out with noble metal catalysts, in acid medium. Additionally, a very low outlay on catalyst, based on the total quantity of reduced formose or formose to be reduced, is necessary.

The process of the instant invention offers all the advantages afforded by the pumping hydrogenation of formose over conventional processes, as described in U.S. application Ser. No. 965,645 such as:

(1) high economy of the process due to the low outlay on catalyst and the short hydrogenation times; (2) low capital outlay due to relatively low hydrogen pressures; (3) extensive splitting of the starting substances into low molecular weight $C_2$ to $C_5$ alcohols so that the viscosity of the polyhydroxyl compounds is reduced, their processibility improved and, at the same time, their compatibility with other substances increased, (this is particularly advantageous for the starting components used in the production of plastics by the polyisocyanate-polyaddition process and in particular relatively high molecular weight polyhydroxyl compounds and blowing agents); (4) the possibility of, if desired, adding other compounds such as, for example, alkanals, monofunctional or polyfunctional ketones, aldehydes or relatively high molecular weight polyols to the formose to be hydrogenated in quantities of up to 50% by weight (based on the total quantity of products to be reduced), since these compounds improve the compatibility of the reaction products with the blowing agents used in the polyisocyanate-polyaddition process; and (5) the possibility of hydrogenating not only formose alone but also including other natural and/or synthetic sugars.

The process according to the invention has the additional major advantage that it yields colorless solutions of polyol mixtures which can be concentrated at temperatures of up to 180° C. without any discoloration.

This is of particular advantage because there are numerous applications for which the polyhydroxyl compounds obtainable by the hydrogenation of formose can only be used following removal of the water serving as solvent. Any discoloration occurring at this stage would be prohibitive, for example, where the polyhydroxyl compounds were to be used as the polyol component in polyurethane lacquers.

Aldehydes and alkanals which may be used with the formoses in the process according to the invention include, in particular, acetaldehyde, propionaldehyde, butyraldehyde, isobutyraldehyde and their methylol derivatives. Suitable ketones include acetone, methylethyl ketone, diethyl ketone, cyclopentanone, cyclohexanone, mesityl oxide, isophorone, acetophenone, benzophenone and their methylol derivatives.

The solvent used in the process according to the invention is primarily water, although the formose may also be dissolved in any monoalcohols or polyalcohols. Suitable alcohols include, for example, methanol, ethanol, propanol, butanol, isopropanol, isobutanol, cyclopentanol, cyclohexanol, 2-ethoxy ethanol, 2-propoxy ethanol, 2-isopropoxy ethanol, 2-butoxy ethanol, 2-(2-methoxyethoxy)ethanol, 2-(2-ethoxyethoxy)-ethanol, 1,2-bis-(2-hydroxyethoxy)-ethane, ethylene glycol, diethylene glycol, triethylene glycol, tetraethylene glycol, 1,2-propane diol, isopropylene glycol, 1,3-propane diol, 1,2-butane diol, 1,3-butane diol, 2-methoxy-1butanol, 2,3-butane diol, 1,5-pentane diol, 2,2-diethyl-1,3-propane diol, 1,6-hexane diol, 2,5-hexane diol, 2-methyl-2,4-pentane diol, 3-methyl-1,5-pentane diol, 3-methyl-2,4-pentane diol, 2,3-dimethyl-2,3-butane diol, 2-methyl-2-propyl-1,3-propane diol, 2,2-diethyl-1,3-propane diol, 2-ethyl-1,3-hexane diol, 2,5-dimethyl-2,5-hexane diol, 2,2,4-trimethyl-1,3-pentane diol, 1,3-diethoxy-2-propanol, 2-hydroxymethyl-2-methyl-1,3-propane diol, 1,2,6-hexane triol, 2-ethyl-2-hydroxymethyl-1,3-propane diol, 2,2-bis-hydroxymethyl-1,3-propane diol, erythritol, quinitol, mannitol, sorbitol and methyl glycoside, also ethoxylation and propoxylation products of these alcohols having a molecular weight of up to about 400 and of course mixtures of these alcohols. Ethylene glycol, glycerol and 1,4-butane diol are particularly preferred.

It is also possible in accordance with the invention to use polyhydroxyl compounds, optionally in admixture with the above mentioned alcohols, for hydrogenating the formose. The polyhydroxyl compounds in question generally have molecular weights of from 400 to 10,000, preferably from 500 to 6000, and are preferably also liquid at room temperature or soluble in the formose solution. Examples of suitable polyhydroxyl compounds include polyesters, polyethers, polythioethers, polyacetals, polycarbonates and polyester amides containing at least 2, generally 2 to 8 but preferably 2 to 4 hydroxyl groups, of the type generally known for the production of homogeneous and cellular polyurethanes.

The hydrogenation process according to the invention may be applied to any formoses of any type. The formose may also be used in admixture with up to 80% by weight, based on the total quantity of compounds to be hydrogenated, of other synthetic or even natural sugars, such as for example glucose, maltose, fructose, saccharose and lactose. In this connection, it is a particular advantage that formose is an excellent solvent or solubility promoter for sugars of this type.

The synthetic invert sugars which may be used in accordance with the invention include hydrolysates of any disaccharides and/or polysaccharides. Examples include cane sugar, mixtures of cane sugar and invert sugars, hydrolysates of trehalose, maltose or isomaltose, hydrolysates of corn and potato starch and of pectins (amylose and amylopectins), cellobiose and lactose, hydrolysates of galatose, glucose mixtures, raffinose hydrolysates, cellulose hydrolysates, hydrolysates of dextrins, optionally in admixture with non-hydrolyzed dextrins, hydrolysates of Schardinger dextrins (cyclic dextrins), hydrolysates of glycogen, hydrolysates of glucose-6-phosphoric acid, hydrolysates of glucose-1-phosphate (Cori esters), fructose-6-phosphate, degraded pectins (polygalacturonic acids), degraded glucosamines and hydrolysates of molasses residues.

The pH-value of the solution to be hydrogenated may be adjusted both with inorganic bases and also with organic bases. It is preferred to use sodium hydroxide, potassium hydroxide, calcium hydroxide, magnesium hydroxide, barium hydroxide, aluminum oxide hydrate, triethylamine, N-methyl morpholine and N-methyl piperidine.

It is particularly preferred to employ the same base used in synthesis of the formose which, before hydrogenation, is converted into the free OH-form by treating the formose solution with ion exchanger resin present in the OH-form, so that the required alkalinity of the formose solution is spontaneously adjusted.

Suitable hydrogenation catalysts for the first stage of the process according to the invention are, in particular, metals having atomic numbers of from 23 to 29, in elemental and/or oxidic form. Suitable catalysts include, for example, catalysts based on nickel or cobalt. The catalysts may be used on substrates of both inorganic materials, such as kieselguhr, silicas, aluminum oxides, alkali and alkaline earth silicates, aluminum silicates, montmorillonite, zeolites, spinels, dolomite, kaolin, magnesium silicates, zirconium oxide, iron oxide, zinc oxide, calcium carbonate, silicon carbide, aluminum phosphate, boron phosphate, asbestos or active carbon, and organic materials, such as naturally occurring or synthetic compounds of high molecular weight, such as silk, polyamides, polystyrene, cellulose or polyurethanes. The substrate may be used for example in the form of beads, strands, filaments, cylinders, polygons or in powder form. Preferred catalysts are Raney-type catalysts, such as Raney nickel, W-1-, W-5-, W-6- and W-7-Raney nickel (cf. H. Adkins, J. Am. Chem. Soc. 69, 3039 (1974)), Raney cobalt catalysts, Raney copper, Raney nickel-iron, Raney cobalt-nickel and Raney cobalt-iron. Other suitable catalysts are metal catalysts produced by the reduction of nickel or cobalt salts, such as Urushibara nickel; nickel or cobalt salts reduced with metal alkyl compounds, alkali hydrides, hydrazine, boronates or boron hydride; catalysts produced by reduction of metal oxides or metal oxide mixtures and also the metal oxides or oxide mixtures themselves.

The catalysts used in the first stage may contain as accelerators one or more of the following elements in quantities of up to 10% by weight: Li, Na, Ca, Ba, K, Ag, Be, La, Ce, V, Nb, Ta, Mo, W and up to 1% by weight of the elements Ru, Rh, Pd, Au, Ir, Pt.

Particularly suitable catalysts include Raney nickel containing up to 90% by weight of Ni and less than 1% by weight of Fe, Ca and Na, Raney nickel-iron containing from 5 to 30% by weight of Fe and less than 1% by weight of Ca and Na and Raney cobalt-iron containing from 10 to 30% by weight of Fe.

Hydrogenation catalysts for the second stage of the process according to the invention are preferably catalysts containing noble metals, particularly metals or mixtures of metals having atomic numbers of 44, 45, 75 and 77. It is particularly preferred to use ruthenium. These metals may be used both in elemental form and also in the form of chemical compounds (for example complex compounds).

According to the invention, however, it is also possible to use mixtures of the four above mentioned metals (or their compounds) with other noble metals as co-catalysts. The noble metal co-catalyst may be used in a quantity of up to 80% by weight (based on the total quantity of catalyst and co-catalyst). Suitable co-catalysts are, for example, Pd, Pt, Os, Ag and Au and compounds of these metals.

Compounds of the catalyst metals suitable for use in accordance with the invention include, in particular, compounds having stable oxidation stages, preferably oxides, oxide hydrates, hydroxides and salts of organic or inorganic acids, but also co-ordination compounds or complex compounds. These classes of compounds representative of all catalyst metals are described in the following with reference to the example of ruthenium: $Ru(OH)_2$; $Ru(OH)_3$; $RuO_2$; $RuCl_3$; $M_2[RuX_5]$; $M_3[RuX_6]$; $M_2[RuO_4]$; $RuCl_2(PPh_3)$; $RuHCl(PPh_3)_3$ or mixtures $RuCl_3/PPH_3$; $[Ru(NH_3)_6]X_3$, $[RuOH(NH_3)_5]X_2$; $[RuY(NH_3)_5]X_2$; $[RuY_2(NH_3)_4]X$ and $[RuCl_3(NH_3)_3]$. In the above formulae, M represents a monovalent metal, preferably an alkali metal, PH represents a phenyl radical and X and Y represent an equivalent of an organic or inorganic acid residue, for example a halogen atom, $CH_3COO$ or $\frac{1}{2}SO_4$.

In general, the second catalyst is also used together with a suitable substrate in the process according to the invention. Suitable catalyst substrates are both inorganic materials, such as kieselguhr, pumice stone, silica, aluminum oxides, alkali and alkaline earth, silicates, aluminum silicates, montmorillonite, bentonite, aluminum silicate clays, kaolinite, zeolites, spinels, dolomite, magnesium silicates, titanium oxide, zirconium oxide, chromium(III)oxide, iron oxide, zinc oxide, alkaline earth sulphates and carbonates, silicon carbide, aluminum phosphate, boron phosphate, asbestos or (active) carbon of any type, and organic materials, for example naturally occurring or synthetic compounds of high molecular weight, such as silk, polyamides, polystyrenes, cellulose, polyurethanes or cation exchanger resins, partly or completely charged with metal. The substrates naturally must be selected in such a way that they neither dissolve nor decompose at the pH-value of the solution to be hydrogenated.

The substrates for the catalysts used in accordance with the invention may assume any form which enables hydrogenation to be carried out on the catalyst, either present in the form of a fixed bed or suspended in the reaction medium.

The support may be present for example in the form of beads, strands, filaments, cylinders, polygons or in powder form. The surface of the reaction vessel may also serve as the substrate.

Catalysts of this type suitable for use in accordance with the invention are known and are described for example in German Offenlegungsschriften Nos. 2,555,856 and 2,536,416; German Auslegeschrift No. 1,082,245 (British Pat. No. 867,689); U.S. Pat. Nos. 2,686,847 and 3,055,440, and by Paul N. Rylander in "Catalytic Hydrogenation over Platinum Metals" Academic Press, New York and London 1967, Chapter I.1 (Platinum Metal Catalysts) and the literature sources cited therein. These publications relate not only to catalysts containing a metal component, but also to mixtures thereof and to mixed catalysts containing up to four active components.

The catalytically active metals and/or their compounds may of course also be used without support materials in the form of a colloidal suspension in the process according to the invention. Homogeneous catalysts such as, for example, the Ru complexes as described in U.S. Pat. No. 3,935,284 are also suitable for use in accordance with the invention. In addition to complexes with low molecular weight complex ligands, it is also possible to use noble metal complexes with long-chain oligomeric or polymeric ligands of the type described for example by E. Bayer and V. Schurig in Chem. Tech. 6 (3), 212/214 (1976). In this case, the active catalyst form is present either in molecular disperse solution or in colloidal solution and may be separated from the product by membrane filtration. "Polymer carriers" of the polyether type or polyethers substituted, for example, by phosphine radicals are preferably used for aqueous and alcoholic media.

The catalyst metals or their catalytically active oxidation stage(s) may be produced in substrate-free form or after application to substrates by reduction of their compounds, preferably their oxides, for example Adams catalysts, in known manner with hydrazine, $B_2H_6$, boron hydride adducts, alkali boranates, alkali hydrides, $SO_2$ and the like, or by prehydrogenation either of the dry oxide or in water (alkaline, neutral or acid pH) or even in non-aqueous solvents (such as alcohols, formitol, and the like). This reduction of the catalyst metal compounds, in the same way as possible activation of the metallic catalysts by reduction, may with advantage be carried out immediately before and in the same apparatus as hydrogenation of the formose, preferably in the solvent in which the formose is dissolved. One advantage of prehydrogenating the catalyst in formitol or in a formitol solution lies in the fact that the product of hydrogenation is not diluted with additional solvent. In addition, this preliminary hydrogenation is preferably carried out under the same conditions (pressure, temperature) as the hydrogenation process according to the invention.

In cases where activation of the catalyst metal or the production thereof from its compounds is carried out in a single step with hydrogenation of the formose, the end products obtained are often undesirably discolored.

The catalysts used in the second stage of the process according to the invention may optionally be activated by the addition of one or more co-catalysts or activators (promoters). The co-catalyst or activator may be added to the formose either separately or together with the catalyst and may be present in dissolved or solid form during hydrogenation. It is of course also possible to fix the activating substance together with the catalyst on the substrate, as for example in the case of the mixed catalysts already described. The catalysts or mixtures of catalysts and the above described co-catalysts used in accordance with the invention may preferably contain as accelerators one or more of the following elements in quantities of up to 10% by weight and preferably in quantities of from 0.1 to 5% by weight (based on the total quantity of catalytically active substance): Li, Na, K, Mg, Ca, Ba, Be, La, Ce, also rare earths, Ti, Zr, V, Nb, Ta, Cr, Mo, W, Fe, Co, Ni and Cu. These activators may also be present either in elemental form or in the form of substantially insoluble compounds, for example in the form of oxides, sulphates, silicates, spinels, phosphates, carbonates (only at pH > 6) or chromates.

Particularly suitable catalysts for the second stage are Ru catalysts on supports such as carbon black, $\gamma$-zeolite or kieselguhr.

The mixtures of polyhydric low molecular weight alcohols produced in accordance with the invention are preferably used as polyol component in the polyisocyanatepolyaddition process.

Accordingly, the present invention also relates to a process for the production of optionally cellular polyurethane plastics by reacting (A) polyisocyanates with (B) compounds containing at least two active hydrogen atoms and having a molecular weight of from 32 to 400, optionally (C) compounds containing at least two active hydrogen atoms and having a molecular weight of from 400 to 10,000 and, optionally, (D) blowing agents, catalysts and other additives known per se, which is characterized in that component (B) comprises mixtures of low molecular weight polyhydric alcohols produced in accordance with the invention.

In producing the polyurethane of the instant invention, aliphatic, cycloaliphatic, araliphatic, aromatic and heterocyclic polyisocyanates of the type known and described for example by W. Siefken in Justus Liebigs Annalen der Chemie, 562, pages 75 to 136 may be used. Examples include those corresponding to the formula $$Q(NCO)_n$$

in which n=2-4, preferably 2, and

Q represents an aliphatic hydrocarbon radical containing from 2 to 18 carbon atoms and preferably from 6 to 10 carbon atoms, a cycloaliphatic hydrocarbon radical containing from 4 to 15, preferably 5 to 10, carbon atoms;

an aromatic hydrocarbon radical containing from 6 to 15 carbon atoms, preferably from 6 to 13 carbon atoms, or an araliphatic hydrocarbon radical containing from 8 to 15 carbon atoms, preferably from 8 to 13 carbon atoms.

Suitable specific examples include ethylene diisocyanate; 1,4-tetramethylene diisocyanate; 1,6-hexamethylene diisocyanate; 1,12-dodecane diisocyanate; cyclobutane-1,3-diisocyanate; cyclohexane-1,3- and -1,4- diisocyanate and mixtures of these isomers; 1-isocyanato-3,3,5-trimethyl-5-isocyanatomethyl cyclohexane (German Auslegeschrift No. 1,202,785, U.S. Pat. No. 3,401,190); 2,4- and 2,6-hexahydrotolylene diisocyanate and mixtures of these isomers; hexahydro-1,3- and/or -1,4-phenylene diisocyanate; perhydro-2,4'- and/or -4,4'-diphenyl methane diisocyanate; 1,3- and 1,4-phenylene diisocyanate; 2,4- and 2,6-tolylene diisocyanate and mixtures of these isomers; diphenyl methane-2,4'- and/or -4,4'-diisocyanate; naphthylene-1,5-diisocyanate; triphenyl methane-4,4',4"-triisocyanate; polyphenyl polymethylene polyisocyanates of the type obtained by condensing aniline with formaldehyde, followed by phosgenation, and described for example in British Pat. Nos. 874,430, and 848,671; m- and p-isocyanatophenyl sulphonyl isocyanates as described in U.S. Pat. No. 3,454,606; perchlorinated aryl polyisocyanates of the type described for example in German Auslegeschrift No. 1,157,601 (U.S. Pat. No. 3,277,138); polyisocyanates containing carbodiimide groups of the type described in German Pat. No. 1,092,007 (U.S. Pat. No. 3,152,162) and in German Offenlegungsschriften Nos. 2,504,400; 2,537,685 and 2,552,350; norbornane diisocyanates as described in U.S. Pat. No. 3,492,330; polyisocyanates containing allophanate groups of the type described for example in British Pat. No. 994,890, in Belgian Pat. No. 761,626 and in Dutch Patent Application No. 7,102,524; polyisocyanates containing isocyanurate groups of the type described for example in U.S. Pat. No. 3,001,973; in German Pat. Nos. 1,022,789; 1,222,067 and 1,027,394 and in German Offenlegungsschriften Nos. 1,929,034 and 2,004,048; polyisocyanates containing urethane groups of the type described for example in Belgian Pat. No. 752,261 or in U.S. Pat. Nos. 3,394,164 and 3,644,457; polyisocyanates containing acylated urea groups as described in German Pat. No. 1,230,778; polyisocyanates containing biuret groups of the type described for example in U.S. Pat. Nos. 3,124,605 and 3,201,372 and in British Pat. No. 889,050; polyisocyanates produced by telomerization reactions of the type described for example in U.S. Pat. No. 3,654,106; polyisocyanates containing ester groups of the type described for example in British Pat. Nos. 965,474 and 1,072,956, in U.S. Pat. No. 3,567,763 and in German Pat. No. 1,231,688; reaction products of the above mentioned isocyanates with acetals as described in German Pat. No. 1,072,385; and polyisocyanates containing polymeric fatty acid residues as described in U.S. Pat. No. 3,455,883.

It is also possible to use the isocyanate-group-containing distillation residues obtained in the commercial production of isocyanates, optionally in solution in one or more of the above mentioned polyisocyanates. It is also possible to use any mixtures of the above mentioned polyisocyanates.

In general, it is particularly preferred to use the readily available polyisocyanates, for example 2,4- and 2,6-tolylene diisocyanate, and any mixtures of these isomers ("TDI"); polyphenyl polymethylene polyisocyanates of the type obtained by condensing aniline with formaldehyde, followed by phosgenation ("crude MDI"); and polyisocyanates containing carbodiimide groups, urethane groups, allophanate groups, isocyanurate groups, urea groups or biuret groups ("modified polyisocyanates"), particularly modified polyisocyanates of the type derived from 2,4- and/or 2,6-tolylene diisocyanate or from 4,4'- and/or 2,4'-diphenyl methane diisocyanate.

As further optional starting components in producing the polyurethanes, are compounds containing at least two isocyanate-reactive hydrogen atoms and generally having molecular weights of from 400 to 10,000. Such compounds may contain amino groups, thiol groups, hydroxyl groups or carboxyl groups. Preferred compounds contain hydroxyl groups, and particularly preferred are compounds containing from 2 to 8 hydroxyl groups and, above all, compounds having molecular weights of from 500 to 6,000, preferably from 1000 to 4000. Suitable examples include polyesters, polyethers, polythioethers, polyacetals, polycarbonates and polyester amides containing at least 2, generally from 2 to 8, but preferably from 2 to 4 hydroxyl groups, of the type generally known for the production of homogeneous and cellular polyurethanes.

The polyesters containing hydroxyl groups suitable for use in accordance with the invention include, for example, reaction products of polyhydric, (preferably dihydric and, optionally, trihydric alcohols), with polybasic, (preferably dibasic), carboxylic acids. Instead of using the free polycarboxylic acids, it is also possible to use the corresponding polycarboxylic acid anhydrides or corresponding polycarboxylic acid esters of lower alcohols or mixtures thereof for producing the polyesters. The polycarboxylic acids may be aliphatic, cycloaliphatic, aromatic and/or heterocyclic and may optionally be substituted, for example by halogen atoms, and/or they may be unsaturated.

Examples of carboxylic acids such as these and their derivatives include succinic acid, adipic acid, suberic acid, azelaic acid, sebacic acid, phthalic acid, isophthalic acid, trimellitic acid, phthalic acid anhydride, tetrahydrophthalic acid anhydride, hexahydrophthalic acid anhydride, tetrachlorophthalic acid anhydride, endomethylene tetrahydrophthalic acid anhydride, glutaric acid anhydride, maleic acid, maleic acid anhydride, fumaric acid, dimerized and trimerized unsaturated fatty acids, which may be in admixture with monomeric unsaturated fatty acids, such as oleic acid; terephthalic acid dimethyl ester and terephthalic acid-bis-glycol ester. Suitable polyhydric alcohols are, for example, ethylene glycol, 1,2- and 1,3-propylene glycol, 1,4- and 2,3-butylene glycol, 1,6-hexane diol, 1,8-octane diol, neopentyl glycol, 1,4-bis-hydroxymethyl cyclohexane, 2-methyl-1,3-propane diol, glycerol, trimethylol propane, 1,2,6-hexane triol, 1,2,4-butane triol, trimethylol ethane, pentaerythritol, quinitol, mannitol and sorbitol, formitol, methyl glycoside, also diethylene glycol, triethylene glycol, tetraethylene glycol and higher polyethylene glycols, dipropylene glycol and higher polypropylene glycols, dibutyl glycol and higher polybutylene glycols. The polyesters may contain terminal carboxyl groups. Polyesters of lactones, for example, ε-caprolactone, or of hydroxy carboxylic acids, for example ω-hydroxy caproic acid, may also be used.

The polyethers containing at least 2, generally 2 to 3 and preferably 2 to 3 hydroxyl groups suitable for use in accordance with the invention are also generally known. They may be obtained for example by polymerizing epoxides, such as ethylene oxide, propylene oxide, butylene oxide, tetrahydrofuran, styrene oxide or epichlorohydrin on their own, for example in the presence of Lewis catalysts, such as boron trifluoride, or by the addition of these epoxides, preferably ethylene oxide and propylene oxide, either as mixtures or successively, with starter components containing reactive hydrogen atoms. Suitable starter components include water, ammonia, alcohols, such as ethylene glycol, 1,3-propylene glycol or 1,2-propylene glycol, trimethylol propane, glycerol, sorbitol, and 4,4'-dihydroxy diphenyl propane, and amines such as aniline, ethanolamine or ethylene diamine. Sucrose polyethers of the type described for example in German Auslegeschriften Nos. 1,176,358 and 1,064,938 and formitol-or formose-started polyethers (German Offenlegungsschriften Nos. 2,639,083 and 2,737,951) may also be used in accordance with the invention. In many cases, it is preferred to use polyethers which contain predominant amounts of primary hydroxyl groups, (up to 90% by weight, based on all the hydroxyl groups present in the polyether). Polybutadienes containing hydroxyl groups are also suitable for use in accordance with the invention.

Among the polythioethers useful, particularly preferred are the condensation products of thiodiglycol on its own and/or with other glycols, dicarboxylic acids, formaldehyde, aminocarboxylic acids or amino alcohols. Depending on the co-components, the products in question are for example polythio mixed ethers, polythioether esters or polythioether ester amides.

Suitable useful polyacetals include, for example, the compounds obtainable from glycols, such as diethylene glycol, triethylene glycol, 4,4'-dioxethoxy diphenyl dimethyl methane, hexane diol and formaldehyde. Polyacetals suitable for use in accordance with the invention may also be obtained by polymerizing cyclic acetals such as, for example, trioxane (German Offenlegungsschrift No. 1,694,128).

Suitable useful polycarbonates containing hydroxyl groups are generally known and can be obtained for example by reacting diols, such as 1,3-propane diol, 1,4-butane diol and/or 1,6-hexane diol, diethylene glycol, triethylene glycol, tetraethylene glycol or thiodiglycol, with diaryl carbonates, for example diphenyl carbonate, or phosgene (German Auslegeschriften Nos. 1,694,080; 1,915,908 and 2,221,751; German Offenlegungsschrift No. 2,605,024).

The useful polyester amides and polyamides include for example the predominantly linear condensates obtained for example from polybasic saturated or unsaturated carboxylic acids or their anhydrides and polyhydric saturated or unsaturated amino alcohols, diamines, polyamines and mixtures thereof.

Polyhydroxyl compounds already containing urethane or urea groups and optionally modified natural polyols, such as castor oil or carbohydrates, such as starch, may also be used. Addition products of alkylene oxides with phenol-formaldehyde resins or even with urea-formaldehyde resins may also be used in accordance with the invention.

Before they are used in the polyisocyanate-polyaddition process, the above mentioned polyhydroxyl compounds may be modified in various ways. Thus, according to German Offenlegungsschriften Nos. 2,210,839 (U.S. Pat. No. 3,849,515) and 2,544,195, a mixture of different polyhydroxyl compounds (for example a polyether polyol and a polyester polyol) may be condensed by etherification in the presence of a strong acid to form a relatively high molecular weight polyol which is made up of different segments attached through ether bridges. It is also possible, for example in accordance with German Offenlegungsschrift No. 2,559,372, to introduce amide groups into the polyhydroxyl compounds or, in accordance with German Offenlegungsschrift No. 2,620,487, to introduce triazine groups by reaction with polyfunctional cyanic acid esters. The reaction of a polyol with a less than equivalent quantity of a diisocyanatocarbodiimide, followed by reaction of the carbodiimide group with an amine, amide, phosphite or carboxylic acid, gives polyhydroxyl compounds containing guanidine, phosphonoformamidine or acyl urea groups (German Offenlegungsschriften Nos. 2,714,289; 2,714,292 and 2,714,293). In some cases, it is of particular advantage to completely or partly convert the relatively high molecular weight polyhydroxyl compounds into the corresponding anthranilic acid esters by reaction with isatoic acid anhydride, as described in German Offenlegungsschriften Nos. 2,019,432 and 2,619,840 and in U.S. Pat. Nos. 3,808,250; 3,975,428 and 4,016,143. Relatively high molecular weight compounds containing terminal aromatic amino groups are obtained in this way.

According to German Offenlegungsschrift No. 2,546,536 and U.S. Pat. No. 3,865,791, relatively high molecular weight compounds containing terminal amino groups are obtained by reacting isocyanate prepolymers with enamines, aldimines or ketimines containing hydroxyl groups, followed by hydrolysis. Further processes for producing relatively high molecular weight compounds containing terminal amino groups or hydrazide groups are described in German Offenlegungsschrift No. 1,694,152 (U.S. Pat. No. 3,625,871).

According to the invention, it is also possible to use polyhydroxyl compounds containing high molecular weight polyadducts and polycondensates or polymers in finely dispersed or dissolved form. Polyhydroxyl compounds such as these are obtained for example by carrying out polyaddition reactions (for example reactions between polyisocyanates and aminofunctional compounds) and polycondensation reactions (for example between formaldehyde and phenols and/or amines) in situ in the above mentioned compounds containing hydroxyl groups. Processes such as these are described for example in German Auslegeschriften Nos. 1,168,075 and 1,260,142 and in German Offenlegungsschriften Nos. 2,324,134; 2,423,984; 2,512,385; 2,513,815; 2,550,796; 2,550,797; 2,550,833; 2,550,862; 2,633,293 and 2,639,254. However, it is also possible, in accordance with U.S. Pat. No. 3,869,413 or German Offenlegungsschrift No. 2,550,860, to mix an aqueous polymer dispersion with a polyhydroxyl compound and subsequently to remove the water from the mixture.

Polyhydroxyl compounds modified by vinyl polymers of the type obtained for example by polymerizing styrene and acrylonitrile in the presence of polyethers (U.S. Pat. Nos. 3,383,351; 3,304,273; 3,523,093 and 3,110,695; German Auslegeschrift No. 1,152,536) or polycarbonate polyols (German Pat. No. 1,769,795; U.S. Pat. No. 3,637,909) are also suitable for use in the process according to the invention. Plastics having particularly good flameproof properties are obtained by using polyether polyols modified in accordance with German Offenlegungsschriften Nos. 2,442,101; 2,644,922 and 2,646,141, by graft polymerization with vinyl phosphonic acid esters and, optionally, (meth) acrylonitrile, (meth)acrylamide or OH-functional (meth) acrylic acid esters. Polyhydroxyl compounds into which carboxyl groups have been introduced by radical graft polymerization with unsaturated carboxylic acids and, optionally, other olefinically unsaturated monomers (German Offenlegungsschriften Nos. 2,714,291; 2,739,620 and 2,654,746) may be used with particular advantage in combination with mineral fillers.

Where modified polhydroxyl compounds of the type mentioned above are used as starting component in the polyisocyanate-polyaddition process, polyurethanes having considerably improved mechanical properties are formed in many cases.

Representatives of the above mentioned compounds in accordance with the invention are known and are described for example in High Polymers, Vol. XVI, "Polyurethanes, Chemistry and Technology", by Saunders-Frisch, Interscience Publishers, New York/London, Vol. I, 1962, pages 32 to 42 and pages 44 to 54 and Vol. II, 1964 pages 5 to 6 and 198 to 199, and in Kunststoff-Handbuch, Vol. VII, Vieweg-Hochtlen, Carl-Hanser-Verlag, Munich, 1966, for example on pages 45 to 71. It is, of course, possible to use mixtures of the above mentioned compounds containing at least two isocyanate-reactive hydrogen atoms and having a molecular weight of from 400 to 10,000, for example, mixtures of polyethers and polyesters.

In some cases, it is of particular advantage to combine low-melting and high-melting polyhydroxyl compounds with one another (German Offenlegungsschrift No. 2,706,297).

Optional starting components for use in producing polyurethanes include compounds containing at least two isocyanate-reactive hydrogen atoms and having molecular weights of from 32 to 400. In this case, too, the compounds in question are compounds containing hydroxyl groups and/or amino groups and/or thiol groups and/or carboxyl groups, preferably compounds containing hydroxyl groups and/or amino groups which serve as chain extenders or crosslinkers. These compounds generally contain from 2 to 8 and preferably from 2 to 4 isocyante-reactive hydrogen atoms. In this case, too, it is possible to use mixtures of different compounds containing at least two isocyanate-reactive hydrogen atoms and having a molecular weight in the range from 32 to 400. Examples of compounds such as these are ethylene glycol, 1,2- and 1,3-propylene glycol, 1,4- and 2,3-butylene glycol, 1,5-pentane diol, 1,6-hexane diol, 1,8-octane diol, neopentyl glycol, 1,4-bis-hydroxymethyl cyclohexane, 2-methyl-1,3-propane diol, dibromobutane diol (U.S. Pat. No. 3,723,392), glycerol, trimethylol propane, 1,2,6-hexane triol, trimethylol ethane, pentaerythritol, quinitol, mannitol and sorbitol, castor oil, diethylene glycol, triethylene glycol, tetraethylene glycol, higher polyethylene glycols having a molecular weight of up to 400, dipropylene glycol, higher polypropylene glycols having a molecular weight of up to 400, dibutyl glycol, higher polybutylene glycols having a molecular weight of up to 400, dibutylene glycol, higher polybutylene glycols having a molecular weight of up to 400, 4,4'-dihydroxy diphenyl propane, dihydroxy methyl hydroquinone, ethanolamine, diethanolamine, N-methyl diethanolamine, triethanolamine and 3-aminopropanol. Solutions of polyisocyanate-polyaddition products, particularly solutions of polyurethane ureas containing ionic groups and/or solutions of polyhydrazodicarbonamides, in low molecular weight polyhydric alcohols may also be used as polyol component in accordance with the invention (German Offenlegungsschrift No. 2,638,759).

Diamines suitable for use in accordance with the invention include, for example, ethylene diamine, 1,4-tetramethylene diamine, 1,11-undecamethylene diamine, 1,12-dodecamethylene diamine and mixtures thereof, 1-amino-3,3,5-trimethyl-5-aminomethyl cyclohexane ("isophorone diamine"), 2,4- and 2,6-hexahydrotolylene diamine and mixtures thereof, perhydro-2,4'- and -4,4'-diaminodiphenyl methane, p-xylylene diamine, bis-(3-aminopropyl)methylamine, diaminoperhydro anthracenes (German Offenlegungsschrift No. 2,638,731) and cycloaliphatic triamines as described in German Offenlegungsschrift No. 2,614,244. It is also possible in accordance with the invention to use hydrazine and substituted hydrazines, for example methyl hydrazine, N,N'-dimethyl hydrazine and their homologs and also acid dihydrazides, for example carbodihydrazide, oxalic acid dihydrazide, the dihydrazides of malonic acid, succinic acid, glutaric acid, adipic acid, β-methyl adipic acid, sebacic acid, hydracrylic acid and terephthalic acid; semicarbazido alkylene hydrazides such as, for example, β-semicarbazido propionic acid hydrazide (German Offenlegungsschrift No. 1,770,591), semicarbazido alkylene carbazinic esters such as, for example, 2-semicarbazido ethyl carbazinic ester (German Offenlegungsschrift No. 1,918,504) or even aminosemicarbazide compounds such as, for example, β-aminoethyl semicarbazido carbonate (German Offenlegungsschrift No. 1,902,931). To control their reactivity, the amino groups may be completely or partly blocked by aldimine or ketimine groups (U.S. Pat. No. 3,734,894; German Offenlegungsschrift No. 2,637,115).

Further examples of diamines are bis-anthranilic acid esters according to German Offenlegungsschriften Nos. 2,040,644 and 2,160,590; 3,5- and 2,4-diaminobenzoic acid esters as described in German Offenlegungsschrift No. 2,025,900; diamines containing ester groups as described in German Offenlegungsschriften Nos. 1,803,635 (U.S. Pat. Nos. 3,681,290 and 3,736,350), 2,040,650 and 2,160,589; diamines containing ether groups as described in German Offenlegungsschriften Nos. 1,770,525 and 1,809,172 (U.S. Pat. Nos. 3,654,364 and 3,736,295); 2-halogen-1,3-phenylene diamines optionally substituted in the 5-position (German Offenlegungsschriften Nos. 2,011,722; 2,025,896 and 2,065,869); 3,3'-dichloro-4,4'-diaminodiphenyl methane; tolylene diamine; 4,4'-diaminodiphenyl methane; 4,4'-diaminodiphenyl disulphides (German Offenlegungsschrift No. 2,404,976); diaminodiphenyl dithio ethers (German Offenlegungsschrift No. 2,509,404); aromatic diamines substituted by alkyl thio groups (German Offenlegungsschrift No. 2,638,760); diaminobenzene phosphonic acid esters (German Offenlegungsschrift No. 2,459,491); aromatic diamines containing sulphonate or carboxylate groups (German Offenlegungsschrift No. 2,720,166); and high-melting diamines as described in German Offenlegungsschrift No. 2,635,400. Examples of aliphatic-aromatic diamines are the aminoalkyl thioanilines described in German Offenlegungsschrift No. 2,734,574.

According to the invention, other suitable chain extenders include such compounds as 1-mercapto-3-aminopropane; amino acids which may be substituted, for example glycine, alanine, valine, serine and lysine; and dicarboxylic acids, which may be substituted, for example, succinic acid, adipic acid, phthalic acid, 4-hydroxy phthalic acid and 4-aminophthalic acid.

In addition, isocyanate-monofunctional compounds may be used as so-called chain terminators in proportions of from 0.01 to 10% by weight, based on polyurethane solids. Monofunctional compounds such as these include monoamines, such as butyl and dibutylamine, octylamine, stearylamine, N-methyl stearylamine, pyrrolidine, piperidine and cyclohexylamine, monoalcohols such as butanol, 2-ethyl hexanol, octanol, dodecanol, the various amyl alcohols, cyclohexanol, ethylene glycol monoethyl ether.

Water and/or readily volatile inorganic or organic substances as blowing agents may also be used in preparing the polyurethane products of the invention. Organic blowing agents include, for example, acetone, ethylacetate, halogen-substituted alkanes, such as methylene chloride, chloroform, ethylidene chloride, vinylidene chloride, monofluorotrichloromethane, chlorodifluoromethane, dichlorodifluoromethane, butane, hexane, heptane or diethyl ether, while inorganic blowing agents include for example, air, carbon dioxide and nitrous oxide. A blowing effect may also be obtained by adding compounds which decompose at temperatures above room temperature giving off gases, such as nitrogen, for example azo compounds such as azodicarbonamide or azoisobutyronitrile. Other examples of blowing agents and information on the use of blowing agents can be found in Kunststoff-Handbuch, Vol. VII, by Vieweg and Hochtlen, Carl-Hanser-Verlag, Munich, 1966, for example on pages 108 and 109, 453 to 455 and 507 to 510.

Catalysts for the urethane reaction may also be used. Examples include tertiary amines, such as triethylamine, tributylamine, N-methyl morpholine, N-ethyl morpholine, N,N,N',N'-tetramethyl ethylene diamine, pentamethyl diethylene triamine and higher homologs (German Offenlegungsschriften Nos. 2,624,527 and 2,624,528), 1,4-diazabicyclo-(2,2,2)-octane, N-methyl-N'-dimethylaminoethyl piperidine, bis-(dimethylaminoalkyl)-piperazines (German Offenlegungsschrift No. 2,636,787), N,N-dimethyl benzylamine, N,N-dimethylcyclohexylamine, N,N-diethyl benzylamine, bis-(N,N-diethylaminoethyl)adipate, N,N,N',N'-tetramethyl-1,3-butane diamine, N,N-dimethyl-β-phenyl ethylamine, 1,2-dimethyl imidazole, 2-methyl imidazole, monocyclic and bicyclic amidines (German Offenlegungsschrift No. 1,720,633), bis-(dialkylamino)-alkyl ethers (U.S. Pat. No. 3,330,782, German Auslegeschrift No. 1,030,558, German Offenlegungsschriften Nos. 1,804,361 and 2,618,280) and tertiary amines containing amide groups (preferably formamide groups) as described in German Offenlegungsschriften No. 2,523,633 and 2,732,292. Suitable catalysts also include Mannich bases of secondary amines, such as dimethylamine, and aldehydes, preferably formaldehyde, or ketones, such as acetone, methylethyl ketone or cyclohexanone, and phenols, such as phenol, nonyl phenol or bisphenol.

Tertiary amines containing isocyanate-reactive hydrogen atoms suitable for use as catalysts include, for example, triethanolamine, triisopropanolamine, N-methyl diethanolamine, N-ethyl diethanolamine, N,N-dimethyl ethanolamine, their reaction products with alkylene oxides, such as propylene oxide and/or ethylene oxide and also secondary-tertiary amines as described in German Offenlegungsschrift No. 2,732,292.

Other suitable catalysts include sila-amines containing carbon-silicon bonds, of the type described for example in German Pat. No. 1,229,290 (corresponding to U.S. Pat. No. 3,620,984). Specific examples include 2,2,4-trimethyl-2-silamorpholine and 1,3-diethylaminomethyl tetramethyl disiloxane.

Other suitable catalysts include nitrogen-containing bases, such as tetraalkyl ammonium hydroxides, alkali hydroxides such as sodium hydroxide, alkali phenolates, such as sodium phenolate, or alkali alcoholates, such as sodium methylate. Hexahydrotriazines may also be used as catalysts (German Offenlegungsschrift No. 1,769,043).

The reaction between NCO-groups and Zerewitinoff-active hydrogen atoms is also greatly accelerated by lactams and azalactams, an associate between the lactam and the compound containing acid hydrogen initially being formed. Associates such as these and their catalytic effect are described in German Offenlegungsschriften Nos. 2,062,288; 2,062,289; 2,117,576 (U.S. Pat. Nos. 3,758,444); 2,129,198; 2,330,175 and 2,330,211.

According to the invention, it is also possible to use organometallic compounds, particularly organo tin compounds, as catalysts for the urethane reaction. In addition to sulphur-containing compounds, such as di-n-octyl tin mercaptide (German Auslegeschrift No. 1,769,367; U.S. Pat. No. 3,654,927), preferred organo tin compounds are tin (II) salts of carboxylic acids, such as tin(II)acetate, tin(II)octoate, tin(II)ethyl hexoate and tin(II)laurate and tin(IV)compounds, for example dibutyl tin oxide, dibutyl tin dichloride, dibutyl tin diacetate, dibutyl tin dilaurate, dibutyl tin maleate or dioctyl tin diacetate.

All the above mentioned catalysts may of course be used in the form of mixtures. In this respect, combinations of organometallic compounds and amidines, aminopyridines or hydrazino pyridines (German Offenlegungsschriften Nos. 2,434,185; 2,601,082 and 2,603,834) are of particular interest.

Further representatives of catalysts suitable for use in accordance with the invention and information on the way in which they work can be found in Kunststoff-Handbuch by Vieweg and Hochtlen, Vol. VII, Carl-Hanser-Verlag, Munich 1966, for example on pages 96 to 102. The catalysts are generally used in a quantity of from about 0.001 to 10% by weight, based on the total quantity of compounds containing at least two isocyanate-reactive hydrogen atoms.

Surface-active additives, such as emulsifiers and foam stabilizers may also be used. Suitable emulsifiers are for example the sodium salts of castor oil sulphonates or salts of fatty acids with amines, such as diethylamine oleate or diethanolamine stearate. Alkali or ammonium salts of sulphonic acids, such as for example dodecyl benzene sulphonic acid or dinaphthyl methane disulphonic acid, or of fatty acids, such as ricinoleic acid, or of polymeric fatty acids may also be used as surface-active additives.

Suitable foam stabilizers include, above all, polyether siloxanes, and particularly water soluble types. The structure of these compounds is generally such that a copolymer of ethylene oxide and propylene oxide is attached to a polydimethyl siloxane residue. Foam stabilizers such as these are described for example in U.S. Pat. Nos. 2,834,748; 2,917,480 and 3,629,308. In many cases, polysiloxane-polyoxyalkylene copolymers branched through allophanate groups as described in German Offenlegungsschrift No. 2,558,523 are of particular interest.

Also usable are reaction retarders, for example acid-reacting substances such as hydrochloric acid or organic acid halides; cell regulators, such as paraffins or fatty alcohols or dimethyl polysiloxanes; pigments or dyes; flameproofing agents such as tris-chloroethyl phosphate, tricresyl phosphate or ammonium phosphate and polyphosphate; stabilizers against the effects of ageing and weather; plasticizers; fungistatic and bacteriostatic substances; as well as fillers such as barium sulphate, kieselguhr, carbon black or whiting.

Further examples of surface-active additives, foam stabilizers, cell regulators, reaction retarders, stabilizers, flameproofing agents, plasticizers, dyes, fillers, fungistatic and bacteriostatic substances which may optionally be used in accordance with the invention and information on the way in which these additives are used and on their respective modes of action can be found in Kunststoff-Handbuch by Vieweg and Hochtlen, Vol. VII, Carl-Hanser-Verlag, Munich 1966, for example on pages 103 to 113.

The process for preparing the urethane products according to the invention is carried out as follows: The reaction components may be reacted by the known one-shot process, by the prepolymer process or by the semi-prepolymer process, in many cases using machines, for example of the type described in U.S. Pat. No. 2,764,565. Particulars of processing machines which may also be used in accordance with the invention can be found in Kunststoff-Handbuch by Vieweg and Hochtlen, Vol. VII, Carl-Hanser-Verlag, Munich, 1966, for example on pages 121 to 205.

In the production of foams, it is also possible in accordance with the invention to carry out foaming in closed molds. To this end, the reaction mixture is introduced into a mold. Suitable mold materials are metals, for example aluminum, or plastics, for example epoxide resin. The foamable reaction mixture foams in the mold and forms the molding. In-mold foaming may be carried out in such a way that the molding has a cellular structure at its surface, although it may also be carried out in such a way that the molding has a compact skin and a cellular core. In this connection, it is possible in accordance with the invention to introduce foamable reaction mixture into the mold in such a quantity that the foam formed just fills the mold. However, it is also possible to introduce into the mold more foamable reaction mixture than is required for filling the interior of the mold with foam. This particular technique is known as overcharging and is described for example in U.S. Pat. Nos. 3,178,490 and 3,182,104.

In many cases, "external" release agents such as silicone oils, are used for in-mold foaming. However, it is also possible to use so-called "internal" release agents, which may be used in admixture with external release agents, of the type known for example described in German Offenlegungsschriften Nos. 2,121,670 and 2,307,589.

According to the invention, it is also possible to produce cold-hardening foams (cf. British Pat. No. 1,162,517 and German Offenlegungsschrift No. 2,153,086). However, it is of course also possible to produce foams by block foaming or by the known laminator process. The exclusive reaction of the polyhydroxyl compounds obtainable in accordance with the invention (i.e. in the absence of other isocyanate-reactive components) with strongly elasticizing polyisocyanates, such as for example biuret polyisocyanates (German Auslegeschrift No. 1,534,178), leads to rigid, light-stable, scratch-resistant and solvent-resistant coatings and lacquers.

In addition, it is possible by subjecting the polyols to base- or acid-catalyzed propoxylation and/or ethoxylation to obtain polyether alcohols of high functionality which, in the case of high hydroxyl numbers, are used for the production of rigid and semi-rigid cellular polyurethane plastics and, in the case of low hydroxyl numbers, as starting materials for highly elastic polyurethane foams. Further particulars on the production of the polyethers are described in German Offenlegungsschrift No. 2,639,083.

By reacting the mixtures of polyhydric alcohols produced in accordance with the invention with polybasic carboxylic acids of the type mentioned above, for example phthalic acid, isophthalic acid, terephthalic acid, tetrahydro and hexahydrophthalic acid, adipic acid or maleic acid by the processes normally used for condensing polyesters, as described for example in Houben-Weyl, Methoden der organischen Chemie, Vol. XIV 12, page 40, it is possible to synthesize highly branched polyesters which, when added to alkyd resins, improve their hardness. The polyesters containing hydroxyl groups which are synthesized from the hydroxyl compounds produced in accordance with the invention may of course also be used as starting components for the production of polyurethane plastics.

The polyhydric alcohols produced in accordance with the invention may also be reacted very easily with long-chain aliphatic monocarboxylic acids, such as caprylic acid, capric acid, lauric acid, myristic acid, palmitic acid, stearic acid, oleic acid, linoleic acid, arachidonic acid or behenic acid and their derivatives, such as for example their methyl or ethyl esters or even their anhydrides and mixed anhydrides, to form esters containing hydroxyl groups. Like ethoxylation products of the polyols or even reaction products of the polyhydroxyl compounds obtainable in accordance with the invention with long-chain monoisocyanates, such as n-octyl, n-decyl, n-dodecyl, myristyl, cetyl or stearyl isocyanate to form carbamic acid esters (cf. for example K. Lindner, Tenside Vol. III, Wissenschaftliche Verlagsgesellschaft Stuttgart, 1964, page 2336), these hydroxyl-containing polyesters are non-ionic surface-active compounds which may be used as valuable emulsifiers, wetting agents or plasticizers. The comounds according to the invention may also be used as humectants in cosmetics and plastics. However, they may also be used for example as antifreeze agents or as formulation aids in the plant protection sector.

The process according to the invention is illustrated by the following Examples in which quantities represent parts by weight and percent by weight, unless otherwise stated.

EXAMPLES

EXAMPLE 1 (Comparison Example)

This Example shows that, although much more time consuming and expensive in regard to the consumption of catalyst, conventional processes give products containing more $C_6$-$C_8$-components than the products obtained by the process according to the invention.

250 ml of a formose solution prepared according to Example 1 of German Offenlegungsschrift No. 2,721,186 are hydrogenated with 80 g of Raney nickel in a 0.7 liter autoclave under a hydrogen pressure of 150 bars first for 4 hours at 30° C., then for 1 hour at 60° C. and finally for 1 hour at 100° C.

A pale yellowish solution of polyhydroxyl compounds containing 0.018% of reducing groups and having the following molecular distribution is obtained:
Compounds containing 2 carbon atoms: 0.8
Compounds containing 3 carbon atoms: 2.2
Compounds containing 4 carbon atoms: 5.6
Compounds containing 5 carbon atoms: 30.4
Compounds containing 6 carbon atoms: 40.0
Compounds containing 7 and more carbon atoms: 21.0

EXAMPLE 2

100 g of catalyst (Raney Ni/Fe in a ratio of 85:15) suspended in 1 liter of water are introduced into a 3 liter capacity fine-steel autoclave and heated to the hydrogenation temperature (150° C.). The remaining space is then filled with hydrogen gas up to the working pressure of 150 bars. 500 ml of a 50% formose solution produced in accordance with Example 1 of German Offenlegungsschrift No. 2,721,186 containing 11.1% of reducible groups (determined as carboxyl groups) are adjusted with sodium hydroxide to a pH-value of 10.0 and pumped into the autoclave over a period of 6 minutes. The mixture is then left to hydrogenate for 6 minutes. 500 ml of the hydrogenated solution are then run off through a riser provided with a frit which retains the catalyst, the next batch is pumped in and hydrogenated in the same way as the first batch. Another 160 batches of 500 ml each are treated in the same way. No loss of catalyst can be determined after this number of cycles. The hydrogenated solutions are collected, desalted over ion exchangers and freed from most of the water present in a thin layer evaporator. A yellow colored formitol having the following properties is obtained:

Residual water content: 1.1%
Residual carbonyl content: 0.016%
OH-number: 1390
Component distribution:
  Compounds containing 2 carbon atoms: 7.9%
  Compounds containing 3 carbon atoms: 22.0%
  Compounds containing 4 carbon atoms: 19.0%
  Compounds containing 5 carbon atoms: 19.1%
  Compounds containing 6 carbon atoms: 21.0%
  Compounds containing 7 and more carbon atoms: 11.0%.

EXAMPLE 3

1.5 g of catalyst (5% by weight, based on the total catalyst weight, of Ru on a support of carbon black) suspended in 1 liter of water are introduced into a 3 liter capacity fine steel autoclave and heated to the hydrogenation temperature of 160° C. under a hydrogen pressure of 120 bars. 500 ml of the non-concentrated 50% formitol solution obtained in accordance with Example 2 are adjusted to pH 4.5 with formic acid, subsequently pumped into the autoclave over a period of 10 minutes and hydrogenated for 60 minutes. 500 ml of solution are then run off through a riser equipped with a frit. Another 150 batches are treated in the same way. No loss of catalyst can be determined.

The hydrogenated solutions are collected, desalted over ion exchangers and freed from water in a thin film evaporator. A crystal clear colorless formitol having the following component distribution is obtained:

Compounds containing 2 carbon atoms: 9.2%
Compounds containing 3 carbon atoms: 21.3%
Compounds containing 4 carbon atoms: 18.8%
Compounds containing 5 carbon atoms: 17.6%
Compounds containing 6 carbon atoms: 20.4%
Compounds containing 7 and more carbon atoms: 11.7%.

EXAMPLE 4

Production of a polyurethane foam:

25 parts of an ethylene-diamine-started polypropylene oxide (OH-number 470),
22 parts of the formitol of Example 3,
10 parts of trichloroethyl phosphate,
15 parts of monofluorotrichloromethane,
0.5 parts of dimethyl benzylamine,
0.5 parts of a standard commercial-grade silicone stabilizer (L-5420, a product of UCC) and
75 parts of a technical phosgenation product of aniline/formaldehyde condensates (NCO-content: 29%)
are mixed intimately and the mixture left to foam in an open mold.

A rigid fine-celled foam of high tensile strength and dimensional stability is obtained.

What is claimed is:

1. A process for the production of low molecular weight polyhydric alcohols by hydrogenating formose solutions in the presence of metal catalysts comprising
   (a) introducing an at least 20% solution of formose, of which the pH-value was adjusted before hydrogenation to a value of from 7.5 to 12.5, in batches into a first reactor in a manner such that the content of reducible groups, determined as carbonyl groups, in the reactor does not exceed a level of 2% by weight;
   (b) hydrogenating the solution in batches in the presence of a first catalyst being selected from the group consisting of metals having atomic numbers of from 23 to 29 and mixtures thereof, said metals, being in elemental and/or oxidic form, the catalyst remaining constant in the reaction and the ratio of formose to said first catalyst in said first reactor being from 3 to 30 times by weight;
   (c) withdrawing the reaction product in batches from the first reactor after the content of reducible groups, determined as carbonyl groups, has fallen to below 1.5% by weight;
   (d) adjusting the pH-value of the reaction product to between 3 and 7;
   (e) introducing said reaction product in batches into a second reactor;
   (f) hydrogenating said reaction product in batches in the presence of a second catalyst said second catalyst remaining constant in the second reactor and being selected from the group consisting of metals having atomic numbers of 44, 45, 75 and 77, compounds thereof, and mixtures thereof, the ratio of the reaction product from step (c) to said second catalyst in said second reactor being from 50 to 5000 times by weight; and
   (g) after a residence time of from 5 minutes to 4 hours withdrawing the reaction product of the second hydrogenation stage in batches from the second reactor.

2. The process of claim 1, characterized in that the individual batches are pumped in the first reactor at a rate sufficient to fill one sixth of the first reactor volume in 3 to 120 minutes.

3. The process of claim 2, characterized in that the rate is such that one sixth of the reactor volume is filled in 5 to 30 minutes.

4. The process of claim 2, characterized in that the individual batches are pumped into the second reactor at a rate sufficient to fill one sixth of the reactor volume in 3 to 120 minutes.

5. The process of claim 4, characterized in that the rate is such that one sixth of the reactor volume is filled in 5 to 30 minutes.

6. The process of claim 2, characterized in that after each batch has been pumped into the first reactor, it is hydrogenated for a period corresponding to between half and four times the pumping in time.

7. The process of claim 6, characterized in that after each batch has been pumped into the second reactor, it is hydrogenated for a period corresponding to between half and 20 times the pumping in time.

8. The process of claim 1, characterized in that up to 80% by weight, based on the total quantity of products to be hydrogenated, of other natural and/or synthetic sugars are introduced with the formose into the first reactor.

9. The process of claim 1, characterized in that a nickel-containing catalyst is used in the first reactor.

10. The process of claim 9, characterized in that Raney nickel, which may be modified with iron and/or zinc, is used as catalyst in the first reactor.

11. The process of claim 9, characterized in that a ruthenium-containing catalyst is used in the second reactor.

12. The process of claim 11, characterized in that ruthenium, which may be modified by palladium, supported by active carbon, is used as the catalyst in the second reactor.

* * * * *